(12) United States Patent
Maini

(10) Patent No.: US 6,354,835 B1
(45) Date of Patent: Mar. 12, 2002

(54) TOOTH SHADE GUIDE

(75) Inventor: Anna Maini, Gaggiano (IT)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/705,488

(22) Filed: Nov. 3, 2000

(30) Foreign Application Priority Data

Nov. 4, 1999 (EP) .............................. 99203640

(51) Int. Cl.⁷ ................................. A61C 19/10
(52) U.S. Cl. ........................ 433/26; 206/63.5
(58) Field of Search ................ 433/26, 203.1; 206/83, 63.5; 229/120.01, 245

(56) References Cited

U.S. PATENT DOCUMENTS

| | | | |
|---|---|---|---|
| 3,094,209 A | * 6/1963 | Krupp | 206/63.5 |
| 3,860,015 A | * 1/1975 | Tarro | 132/82 |
| 4,207,678 A | 6/1980 | Jeannette | 433/203 |
| 4,919,617 A | 4/1990 | Antons et al. | 433/26 |
| 5,222,657 A | 6/1993 | Holland, Jr. | 229/103 |
| 5,692,900 A | * 12/1997 | Fischer | 433/26 |
| 5,826,785 A | * 10/1998 | Belvederi et al. | 229/162 |

OTHER PUBLICATIONS

WPI Abstract Accession No. 1994–282600/35 & JP 6209959A (Kanebo Ltd.) Feb. 8, 1994.

* cited by examiner

Primary Examiner—John J. Wilson
Assistant Examiner—Melba Bumgarner
(74) Attorney, Agent, or Firm—Milton L. Honig

(57) ABSTRACT

A tooth shade guide device and package combination comprises a device frangibly attached to the package.

6 Claims, 1 Drawing Sheet

TOOTH SHADE GUIDE

BACKGROUND OF THE INVENTION

1. Field of the Invention

The present invention concerns a tooth shade guide device and packaging combination wherein the guide device and package are frangibly attached to one another.

2. The Related Art

Shade guide devices for self and professional assessment of the color of teeth are well known in the art. Some shade guides are designed to be used by manufacturers of false teeth where the desired tooth color is measured and then recorded to match the false tooth with neighbouring natural teeth. An example of such a device is disclosed in U.S. Pat. No. 4,207,678 (Jeanette) which describes a dental shade holder and individual shade guides which individually represent different shades. To obtain a comparison between a natural tooth and an artificial tooth a dental practitioner selects which guide corresponds more closely to the color of the natural tooth and then identifies a false tooth accordingly. The differently colored shade guides are arranged along a single side of the holder and may be arranged in any specific order of color.

Another shade guide device is disclosed in U.S. Pat. No. 4,919,617 (Antons) which describes a similar holder with a plurality of shade guides attached along one side of said holder. The individual shade guides are attached to the holder by way of a finger which is perforated. This allows for removal of the guide to allow for improved comparison with the natural tooth.

Shade guide devices comprising a more basic lay out are also known in the art and are included in several tooth-whitening products to allow the user to self assess the colour of his teeth.

Such devices usually consist of a handle on which is displayed varying shades of white, usually ranging from perfect white to a dark cream colour. The guides are included in the packaged product and have to be manufactured separately from the remainder of the package and included when the contents of the product are packaged together before shipping.

SUMMARY OF THE INVENTION

Accordingly, the present invention provides a tooth shade guide device and package combination, characterised in that the guide device and the package are frangibly attached to one another.

By package is meant the outer packaging of a product, for example, the outer cardboard packaging which is usually discarded soon after purchase.

It is an essential feature of the invention that the package is frangibly attached to the shade guide. In this way the guide can be removed from the packaging and used to assess the shade of the teeth later.

The guide is preferably attached by way of a perforated link thus allowing the guide and package to be manufactured in one piece but it is conceivable for the two to be attached after manufacture through the use of an adhesive.

According to a further aspect the invention provides a blank capable of being formed into a package suitable for use as a toothpaste package and additionally comprising a shade guide frangibly attached thereto.

BRIEF DESCRIPTION OF THE DRAWING

The invention shall now be described with reference to the figures in which.

DETAILED DESCRIPTION OF THE INVENTION

Figure 1:
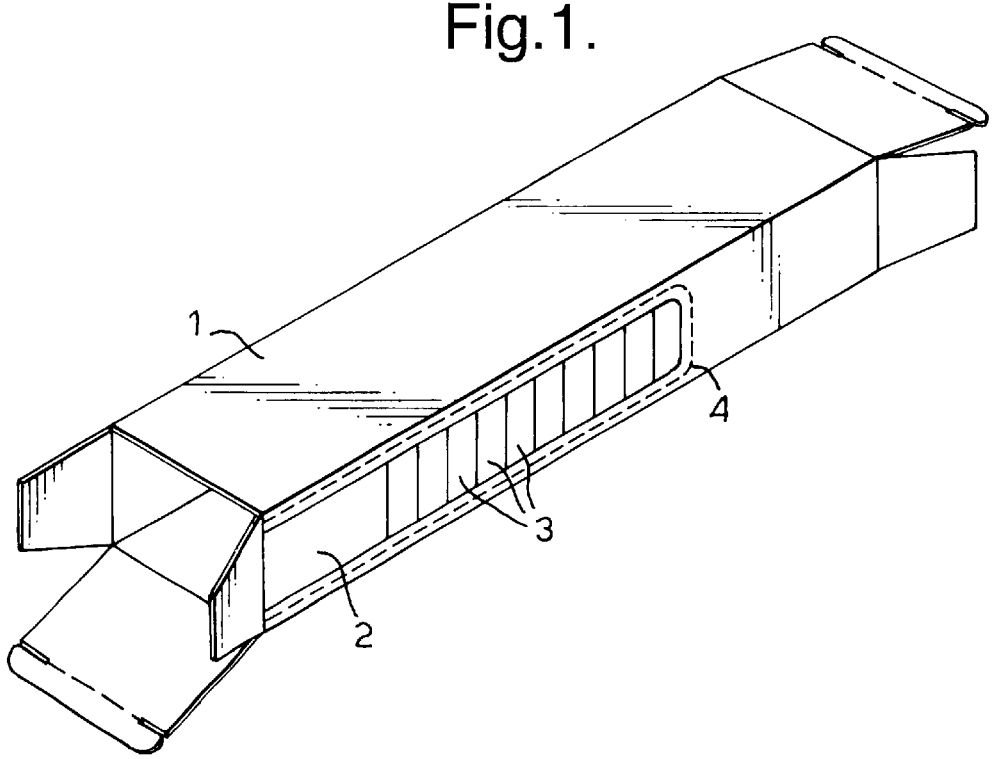
FIG. 1 is a plan perspective view of a toothpaste package with a shade guide.

FIG. 1 shows a tooth shade guide device 2 and package 1 combination wherein the shade guide comprises a plurality of individual shade guides 3 to enable self assessment of the color of the teeth. The device 2 is in the form of a perforated portion 4 which is frangibly removable from the remainder of the package.

Figure 2:
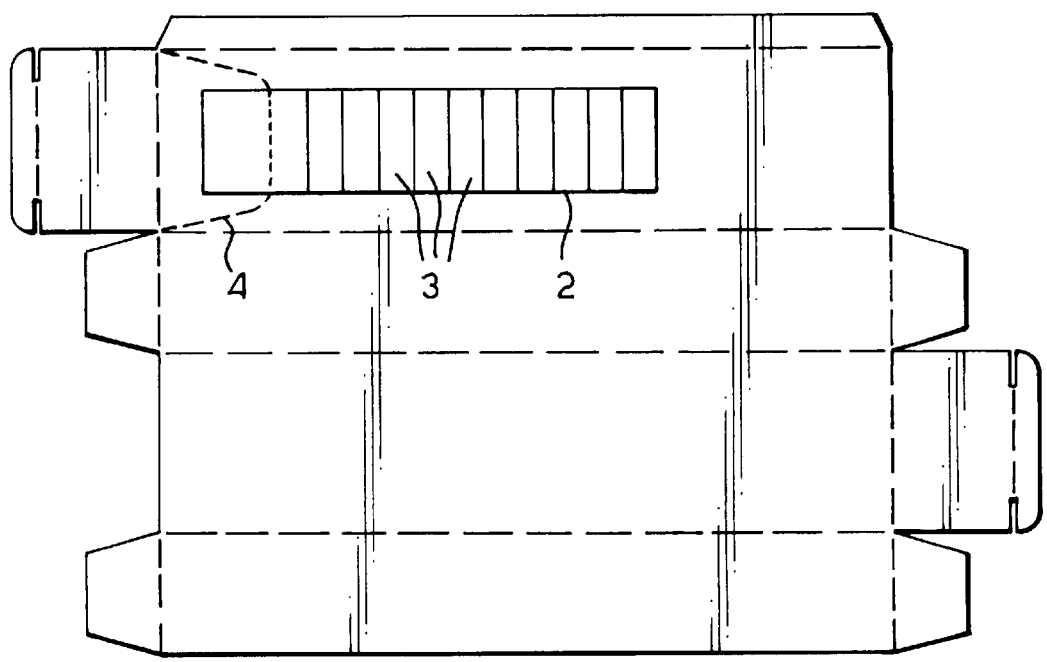
FIG. 2 is a package blank of a second embodiment of a toothpaste package with shade guide.

FIG. 2 shows a blank capable of forming a tooth shade guide device and package combination wherein the device is attached to the blank with an adhesive. The portion of the blank attached to the device is capable of being torn off from the remainder of the package to release a shade guide device ready for use.

What is claimed is:

1. A toothpaste product comprising a package and a toothpaste held within the package, the package comprising a tooth shade guide device frangibly attached to a wall of the package.

2. The toothpaste product according to claim 1 wherein the tooth shade guide device forms a portion of the package wall, the portion being delineated by perforations allowing the device to be torn-off from the package.

3. The toothpaste product according to claim 1 wherein the tooth shade guide is adhesively attached to a wall of the package.

4. A blank for a toothpaste product package comprising:

first, second, third and fourth panels unitarily forming the blank and each defined by at least one crease line, the first panel comprising a tooth shade guide device frangibly attached thereto, the device comprising a plurality of individual shade guides ranging in color from perfect white to a dark cream color.

5. The blank according to claim 4 wherein the tooth shade guide device is separable from the first panel by tear-off along a perforation line.

6. The blank according to claim 4 wherein the tooth shade guide device is adhesively attached to the first panel.

* * * * *